United States Patent
Halsmer et al.

(10) Patent No.: US 7,566,170 B2
(45) Date of Patent: Jul. 28, 2009

(54) SYSTEMS, METHODS AND APPARATUS OF AN IMAGE RECEPTOR ARM

(76) Inventors: Matthew Aaron Halsmer, 411 Harvey Ave., Waukesha, WI (US) 53186; Jonathon Carl Boomgaarden, 900 Michigan Ave., Waukesha, WI (US) 53188

(*) Notice: Subject to any disclaimer, the term of this patent is extended or adjusted under 35 U.S.C. 154(b) by 101 days.

(21) Appl. No.: 11/690,096

(22) Filed: Mar. 22, 2007

(65) Prior Publication Data

US 2008/0232552 A1 Sep. 25, 2008

(51) Int. Cl.
*G03B 42/02* (2006.01)
(52) U.S. Cl. .................. 378/189; 378/167; 378/181
(58) Field of Classification Search .......... 378/167, 378/181, 189, 196, 197, 198; 248/370, 421; 74/521
See application file for complete search history.

(56) References Cited

U.S. PATENT DOCUMENTS

| | | | | |
|---|---|---|---|---|
| 2,697,845 | A * | 12/1954 | Broner | 14/45 |
| 3,155,383 | A | 11/1964 | Whitmore | |
| 3,784,837 | A * | 1/1974 | Holmstrom | 378/189 |
| 4,021,715 | A | 5/1977 | Von Hacht et al. | |
| 4,381,787 | A * | 5/1983 | Hottinger | 600/443 |
| 4,426,725 | A * | 1/1984 | Grady | 378/196 |
| 4,630,872 | A | 12/1986 | Teramachi | |
| 4,671,728 | A | 6/1987 | Clark et al. | |
| H000313 | H | 7/1987 | Staudenmann et al. | |
| 4,769,565 | A | 9/1988 | Teramachi | |
| 4,894,855 | A * | 1/1990 | Kresse | 378/196 |
| 5,048,069 | A | 9/1991 | Sizcek | |
| 5,050,202 | A | 9/1991 | Yanome | |
| 5,157,707 | A | 10/1992 | Ohlson | |
| 5,388,913 | A | 2/1995 | Cawley et al. | |
| 5,485,763 | A * | 1/1996 | Pincus | 74/521 |
| 5,506,879 | A | 4/1996 | Mori et al. | |
| 5,521,957 | A * | 5/1996 | Hansen | 378/198 |
| 5,636,259 | A | 6/1997 | Khutoryansky et al. | |
| 5,658,078 | A | 8/1997 | Cawley | |
| 5,671,266 | A | 9/1997 | Linhart | |
| 5,751,788 | A | 5/1998 | Khutoryansky et al. | |
| 5,768,336 | A | 6/1998 | Khutoryansky et al. | |
| 5,870,450 | A | 2/1999 | Khutoryansky et al. | |
| 5,917,882 | A | 6/1999 | Khutoryansky et al. | |
| 6,123,638 | A * | 9/2000 | Butterfield | 474/245 |
| 6,128,006 | A | 10/2000 | Rosenberg et al. | |
| 6,155,716 | A | 12/2000 | Okamura et al. | |
| 6,200,024 | B1 * | 3/2001 | Negrelli | 378/197 |
| 6,240,582 | B1 | 6/2001 | Reinke | |
| 6,282,264 | B1 | 8/2001 | Smith et al. | |
| 6,435,715 | B1 * | 8/2002 | Betz et al. | 378/197 |
| 6,459,226 | B1 | 10/2002 | Zettel et al. | |
| 6,552,499 | B2 | 4/2003 | Derra et al. | |

(Continued)

OTHER PUBLICATIONS

Kodak, Kodak Directview DR 7500 System, Feb. 2, 2007.

*Primary Examiner*—Allen C. Ho
(74) *Attorney, Agent, or Firm*—William Baxter; Ellis B. Ramirez; Michael G. Smith

(57) ABSTRACT

Systems, methods and apparatus are provided through which in some embodiments, a medical imaging apparatus includes a medical image receptor, a wallstand, and a mechanism that provides at least 3 degrees of freedom. The mechanism is operably coupled to the medical image receptor and the mechanism is operably coupled to the wallstand.

20 Claims, 9 Drawing Sheets

U.S. PATENT DOCUMENTS

| | | |
|---|---|---|
| 6,582,121 B2 * | 6/2003 | Crain et al. ................. 378/197 |
| 6,601,826 B1 * | 8/2003 | Granata ...................... 254/122 |
| 7,177,393 B2 | 2/2007 | Kanemitsu |
| 7,401,977 B2 * | 7/2008 | Graumann et al. .......... 378/205 |
| 2002/0112016 A1 | 8/2002 | Peshkin et al. |
| 2003/0095635 A1 | 5/2003 | Moritake et al. |
| 2004/0131159 A1 | 7/2004 | McKenna |

* cited by examiner

SYSTEMS, METHODS AND APPARATUS OF AN IMAGE RECEPTOR ARM

FIELD OF THE INVENTION

This invention relates generally to medical imaging wallstands, and more particularly to an arm to couple an image receptor to the wallstand.

BACKGROUND OF THE INVENTION

When medical image receptors image a part of a human body, the exact position of the image receptors can be very important. Quite often, the position of the image receptors is precisely planned beforehand, and slight deviations in the position can render images taken while the image receptor is slightly mis-positioned are greatly reduced value in diagnosis and treatment of ailments.

In order to provide stable and precise positioning, quite often the image receptors are coupled to wallstands. Coupling the image receptor to the wallstand provides a mechanically stable support for the image receptor, which in turn improves the ability of an operator to precisely position the image receptor.

Conventional wallstand receptors have at most 2 degrees of freedom: one degree of freedom which is in the vertical direction and the other degree of freedom which is a tilting of the receptor from a vertical plane to a horizontal plane. The limited degrees of freedom limits the ability to quickly and easily position the image receptor.

Having a minimal size of the image receptor and the coupling of the receptor to the wallstand is also highly valued. For example, a small size of the equipments helps to position the image receptor under a removable stretcher table. Positioning the image receptor creates the need for telescoping coupling or other technology that pulls the receptor back towards the wall for most usage and then extends the receptor to reach under a table when needed.

Other degrees of freedom are also increasingly appreciated. The other degrees of freedom include pivoting the detector about the vertical axis and a panning of the receptor side to side.

For the reasons stated above, and for other reasons stated below which will become apparent to those skilled in the art upon reading and understanding the present specification, there is a need in the art for an improved range of motion of an image receptor that is operably coupled to a wallstand. There is also a need for a simpler structure.

BRIEF DESCRIPTION OF THE INVENTION

The above-mentioned shortcomings, disadvantages and problems are addressed herein, which will be understood by reading and studying the following specification.

In one aspect, a wallstand arm includes a 6 link planar mechanism that is arranged such that two sets of two-link arms connect a vertical carriage on the column to a medical image receptor.

In another aspect, a medical imaging apparatus includes a medical image receptor, a wallstand, and a mechanism providing at least 3 degrees of freedom, the mechanism operably coupled to the medical image receptor and the mechanism operably coupled to the wallstand.

In yet another aspect, an apparatus to operable to couple a medical image receptor to a wallstand includes a first articulated arm, the first articulated arm being operably coupled by a first pivot. The apparatus also includes a second articulated arm, the second articulated arm being operably coupled by a second pivot. The first articulated arm is operable to couple to the second articulated arm through the medical image receptor. The first articulated arm is operable to couple to the second articulated arm through the wallstand.

In still another aspect, a computer-accessible medium includes executable instructions to position a medical X-ray image receptor. The executable instructions are capable of directing a processor to receive an indication that a drive is disengaged from a wallstand apparatus, the drive having a clutch and an encoder, the wallstand apparatus having a first articulated arm having at least three degrees of freedom, the first articulated arm being on a same plane as a second articulated arm, the second articulated arm. The executable instructions are capable of directing a processor to receive a position from the encoder, determine a coordinated position of the first articulated arm and the second articulated arm, send at least one signal to a drive that is operably coupled to the first articulated arm to move the first articulated arm into the coordinated position, and send at least one signal to a drive that is operably coupled to the second articulated arm to move the second articulated arm into the coordinated position.

Apparatus, systems, and methods of varying scope are described herein. In addition to the aspects and advantages described in this summary, further aspects and advantages will become apparent by reference to the drawings and by reading the detailed description that follows.

DETAILED DESCRIPTION OF THE INVENTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

The detailed description is divided into five sections. In the first section, a system level overview is described. In the second section, apparatus of embodiments are described. In the third section, embodiments of methods are described. In the fourth section, a hardware and the operating environment in conjunction with which embodiments may be practiced are described. Finally, in the fifth section, a conclusion of the detailed description is provided.

System Level Overview

Figure 1:
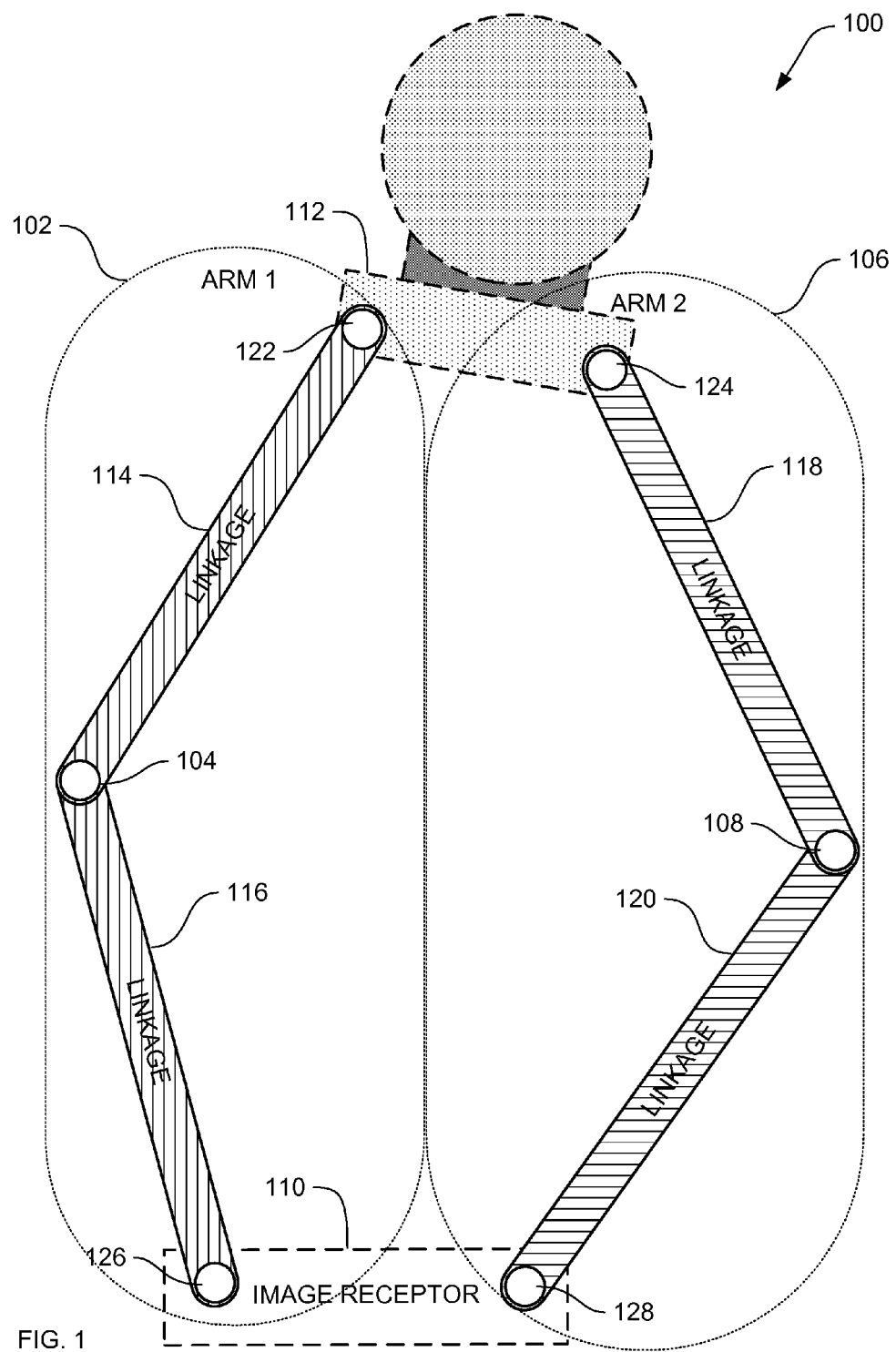
FIG. 1 is a top-view block diagram of an overview of a system to operably couple a medical image receptor to a wallstand.

FIG. 1 is a top-view block diagram of an overview of a system 100 to operably couple a medical image receptor to a wallstand. The system level overview of the operation of an embodiment is described in this section of the detailed description. System 100 solves the need in the art for an improved range of motion of a medical image receptor that is operably coupled to a wallstand.

System 100 includes a first articulated arm 102 (arm 1). The first articulated arm 102 is articulated by a first pivot 104.

System 100 includes also includes a second articulated arm 106 (arm 2), the second articulated arm 106 is articulated by a second pivot 108.

In some embodiments of system 100, the first articulated arm 102 is operably coupled to the second articulated arm 106 through a medical image receptor 110. In some embodiments of system 100, the first articulated arm 102 is operably coupled to the second articulated arm 106 through a wallstand 112.

In some embodiments of system 100, the first articulated arm 102 and the second articulated arm 106 are articulated in the same plane. More specifically, the first pivot 104 is aligned in the same plane as the second pivot 108. The plane of articulation is illustrated from a different perspective in FIG. 6.

In some embodiments of system 100, each arm (arm 1 102 and arm 2 106) each include two articulated linkages, 114, 116 118 and 120. Two articulated linkages in each arm provide three degrees of freedom.

Gruebler's equation is used to calculate the degrees of freedom of planar, closed linkages. The number of degrees of freedom of a linkage is also called its mobility. Gruebler's equation follows in table 1:

$$m=3(n-1)-2f \qquad \text{Table 1}$$

In Gruebler's equation, m=mobility=degrees of freedom, n=number of links (including a single ground link) and f=number of one degree of freedom joints (pin or slider joints). System 100 includes six linkages: the medical image receptor 110, the wallstand 112 and the articulated linkages 114, 116 118 and 120. Therefore, the number of links (n) in system 100 is 6. System 100 includes six freedom joints: the first pivot 104, the second pivot 108 and pivots 122, 124, 126 and 128. Therefore the number of one degree of freedom joints (f) in system 100 is 6. As a result, Gruebler's equation indicates that the degrees of freedom (m) of system 100 is three (3). Some embodiments of pivots 104, 108, 122, 124, 126 and 128 can include bearings or thrust bearings to provide low-friction movement of the pivots.

The articulated linkages of system 100 that provide three degrees of freedom yields a high degree of mobility of the medical image receptor 110, which in turn solves the need in the art for an improved range of motion of a medical image receptor. Not only does system 100 have an improved range of motion, but system 100 also has a simple structure.

While the system 100 is not limited to any particular first articulated arm 102, first pivot 104, second articulated arm 106, second pivot 108, medical image receptor 110, wallstand 112, articulated linkages, 114, 116 118 and 120 and pivots 122, 124, 126 and 128, for sake of clarity a simplified first articulated arm 102, first pivot 104, second articulated arm 106, second pivot 108, medical image receptor 110, wallstand 112, articulated linkages, 114, 116 118 and 120 and pivots 122, 124, 126 and 128 are described.

In subsequent figures, system 100 is shown in various positions, and an apparatus having 5 degrees of freedom is shown below in FIG. 5.

Apparatus Embodiments

In the previous section, a system level overview of the operation of an embodiment was described. In this section, the particular apparatus of such an embodiment are described by reference to a series of diagrams.

Figure 2:
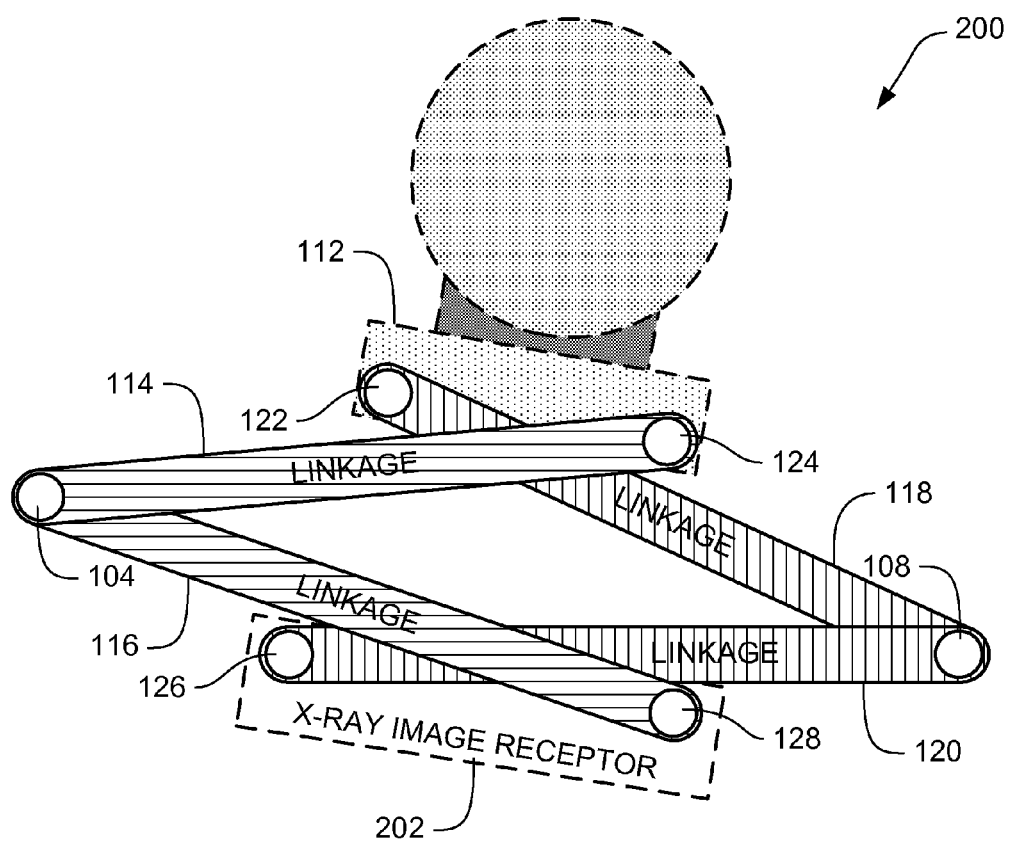
FIG. 2 is a top-view block diagram of an apparatus to operably couple a medical image receptor to a wallstand in which arms of the apparatus are nearly fully retracted and the arms cross each other twice.

FIG. 2 is a top-view block diagram of an apparatus 200 to operably couple a medical image receptor to a wallstand in which arms of the apparatus are nearly fully retracted and the arms cross each other twice. Apparatus 200 solves the need in the art for an improved range of motion of a medical image receptor that is operably coupled to a wallstand.

Apparatus 200 includes all of the same components as system 100 in FIG. 1, above with one variation in the apparatus from FIG. 1: the medical image receptor is a medical X-ray image receptor 202. The medical image receptor 110 of FIGS. 1 and 3-7 can be operated with the medical X-ray image receptor 202.

The arms (not numbered in FIG. 2) and articulated linkages of apparatus 200 cross each other twice between the medical X-ray image receptor 202 and the wallstand 112. More specifically, the articulated linkages 114 and 118 cross each other and the articulated linkages 116 and 120 cross each other. Apparatus 200 has a decreased footprint when the medical X-ray image receptor 202 is retracted.

Gruebler's equation indicates that apparatus 200 has three (3) degrees of freedom. The three (3) degrees of freedom provides a high degree of mobility of the medical X-ray image receptor 202, which in turn solves the need in the art for an improved range of motion of a medical image receptor. Not only does apparatus 200 have an improved range of motion, but apparatus 200 also has a simple structure. FIG. 2 shows that these three degrees of freedom can generate a quite small size when fully retracted.

Figure 3:
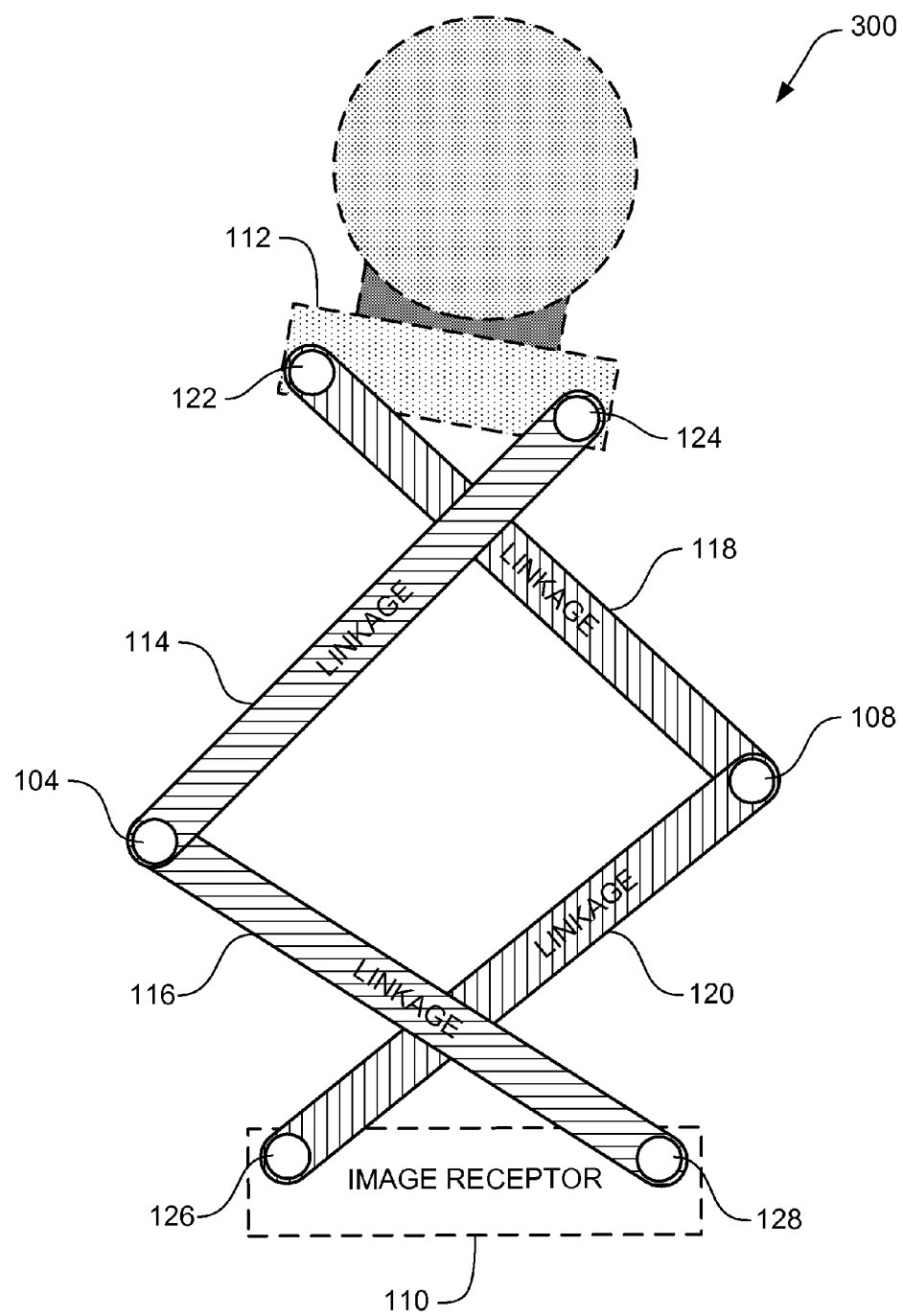
FIG. 3 is a top-view block diagram of an apparatus to operably couple a medical image receptor to a wallstand in which arms of the apparatus are nearly fully extended and the arms cross each other twice.

FIG. 3 is a top-view block diagram of an apparatus 300 to operably couple a medical image receptor to a wallstand in which arms of the apparatus are nearly fully extended and the arms cross each other twice. Apparatus 300 solves the need in the art for an improved range of motion of a medical image receptor that is operably coupled to a wallstand.

Apparatus 300 includes all of the same components as system 100 in FIG. 1, above. The arms (not numbered in FIG. 3) and articulated linkages of apparatus 300 cross each other twice between the medical image receptor 110 and the wallstand 112. More specifically, the articulated linkages 114 and 118 cross each other and the articulated linkages 116 and 120 cross each other.

Gruebler's equation indicates that apparatus 300 has three (3) degrees of freedom. The three (3) degrees of freedom provides a high degree of mobility of the medical image receptor 110, which in turn solves the need in the art for an improved range of motion of a medical image receptor. Not only does apparatus 300 have an improved range of motion, but apparatus 300 also has a simple structure. FIG. 3 shows that these three degrees of freedom can generate a quite long arm when extended.

System 100 and apparatus 200 and 300 are the same device, the only difference between the figures being the position of the arms and articulated linkages. Each articulated linkage rotates about the pivots. The rotation provides a total of three degrees of freedom in these arm assemblies.

Figure 4:
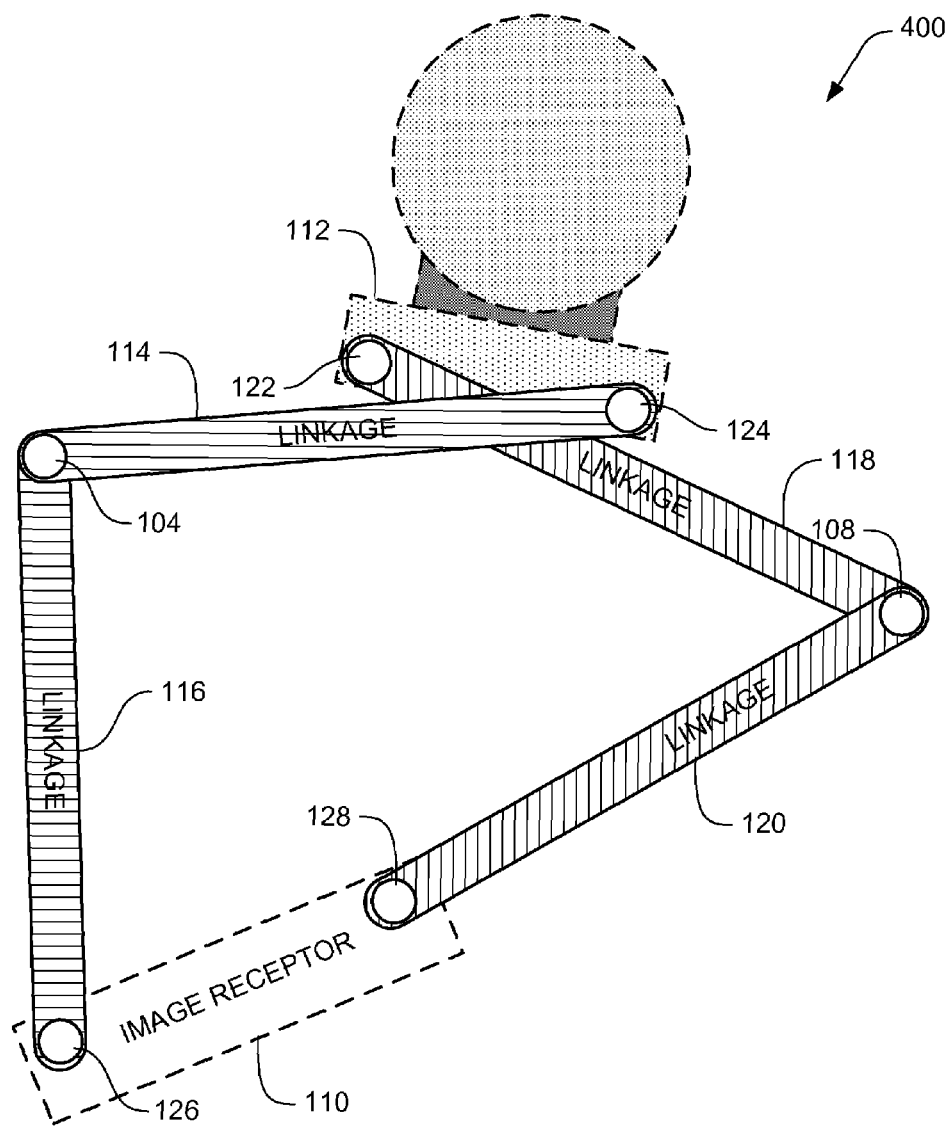
FIG. 4 is a top-view block diagram of an apparatus to operably couple a medical image receptor to a wallstand in which arms of the apparatus are nearly fully extended and the arms cross each other once.

FIG. 4 is a top-view block diagram of an apparatus 400 to operably couple a medical image receptor to a wallstand in which arms of the apparatus are nearly fully extended and the arms cross each other once. Apparatus 400 solves the need in the art for an improved range of motion of a medical image receptor that is operably coupled to a wallstand.

Apparatus 400 includes all of the same components as system 100 in FIG. 1 and apparatus 200 above. The arms (not numbered in FIG. 4) and articulated linkages of apparatus 400 cross each other once between the medical image receptor 110 and the wallstand 112. More specifically, the articulated linkages 114 and 118 cross each other and the articulated linkages 116 and 120 do not cross each other.

Gruebler's equation indicates that apparatus 400 has three (3) degrees of freedom. The three (3) degrees of freedom provides a high degree of mobility of the medical image receptor 110, which in turn solves the need in the art for an improved range of motion of a medical image receptor. Not only does apparatus 400 have an improved range of motion, but system 100 also has a simple structure. FIG. 4 shows that these three degrees of freedom can generate panning and twisting capability of the position of the medical image receptor 110.

Figure 5:
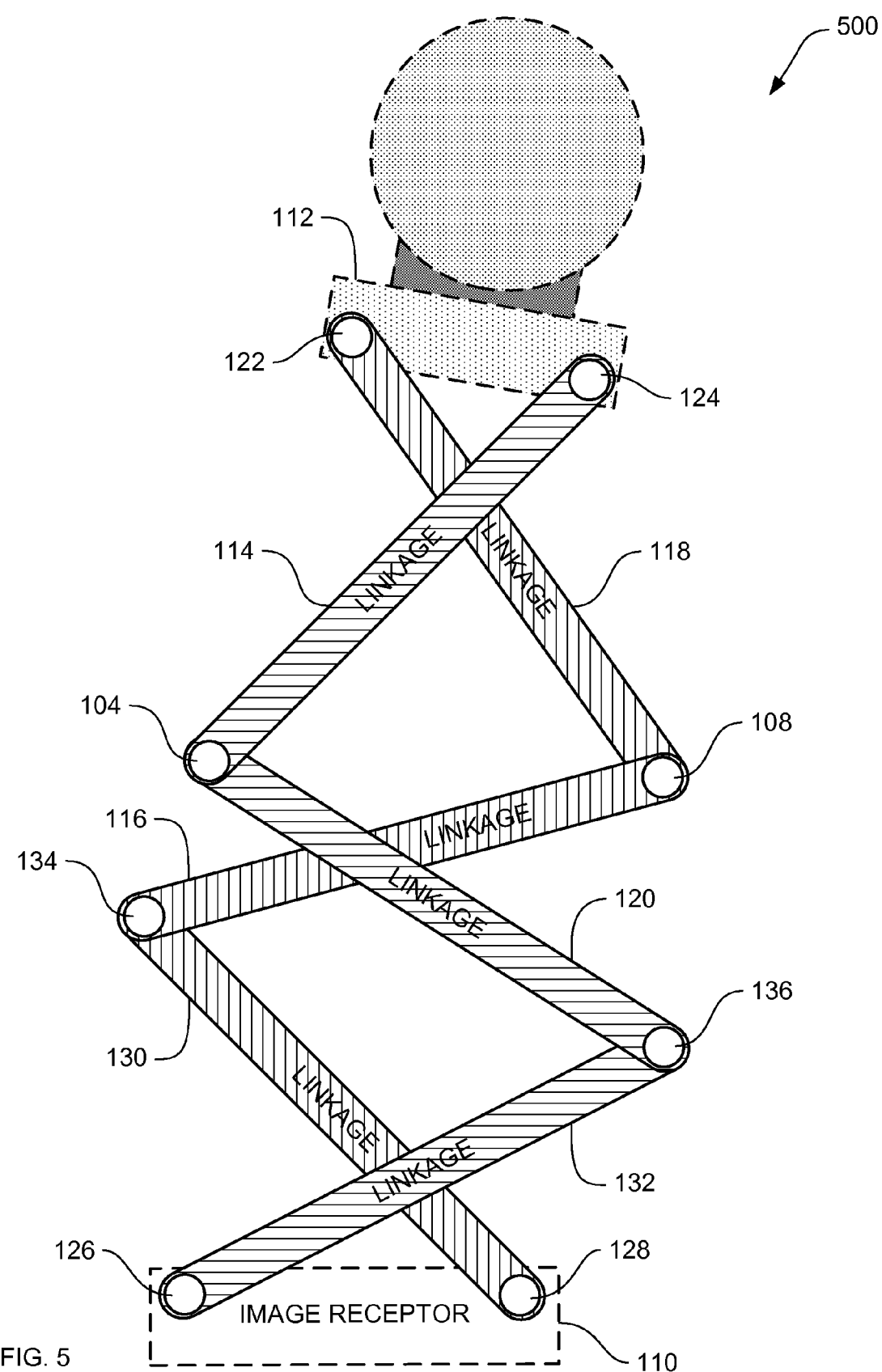
FIG. 5 is a top-view block diagram of an apparatus having five degrees of freedom to operably couple a medical image receptor to a wallstand in which two arms having at least six articulated linkages of the apparatus are nearly fully extended and the arms cross each other thrice.

FIG. 5 is a top-view block diagram of an apparatus 500 having five degrees of freedom to operably couple a medical image receptor to a wallstand in which two arms having at least six articulated linkages of the apparatus are nearly fully extended and the arms cross each other thrice. Apparatus 500 solves the need in the art for an improved range of motion of a medical image receptor that is operably coupled to a wallstand.

Apparatus 500 includes all of the same components as system 100 in FIG. 1, above, including at least two additional articulated linkages 130 and 132 and pivots 134 and 136. The arms (not numbered in FIG. 5) and articulated linkages of apparatus 500 cross each other thrice between the medical image receptor 110 and the wallstand 112. More specifically, the articulated linkages 114 and 118 cross each other, the articulated linkages 116 and 120 cross each other and the articulated linkages 130 and 132 cross each other.

In Gruebler's equation in Table 1 above, m=mobility=degrees of freedom, n=number of links (including a single ground link) and f=number of one degree of freedom joints (pin or slider joints). Apparatus 500 includes eight linkages: the medical image receptor 110, the wallstand 112 and the articulated linkages 114, 116 118, 120, 130 and 132. Therefore, the number of links (n) in system 100 is eight (8). Apparatus 500 includes eight freedom joints: the first pivot 104, the second pivot 108 and pivots 122, 124, 126, 128, 134 and 136. Therefore the number of one degree of freedom joints (f) in system 100 is eight. As a result, Gruebler's equation indicates that the degrees of freedom (m) of system 100 is five (5).

The articulated linkages of apparatus 500 that provide three degrees of freedom yields a high degree of mobility of the medical image receptor 110, which in turn solves the need in the art for an improved range of motion of a medical image receptor. Not only does apparatus 500 have an improved range of motion, but apparatus 500 also has a simple structure.

In some embodiments of system 100 and apparatus 200, 300 and 400, a tilting mechanism (not shown) is operably coupled between articulating linkages 116 and 120 and the medical image receptor 110 that provides vertical movement of the medical image receptor 110 on the column assembly yielding a wallstand that has a total of 5 degrees of freedom. In some embodiments of apparatus 500, a tilting mechanism is operably coupled between articulating linkages 116 and 120 and the medical image receptor 110 that provides vertical movement of the medical image receptor 110 on the column assembly yielding a wallstand that has a total of 7 degrees of freedom. Other embodiments that are not shown include more articulating linkages than shown in the figures. For example, some embodiments not shown include eight (8) articulating linkages. Alternatives include a serial type cascading of one degree of freedom at a time.

Figure 6:
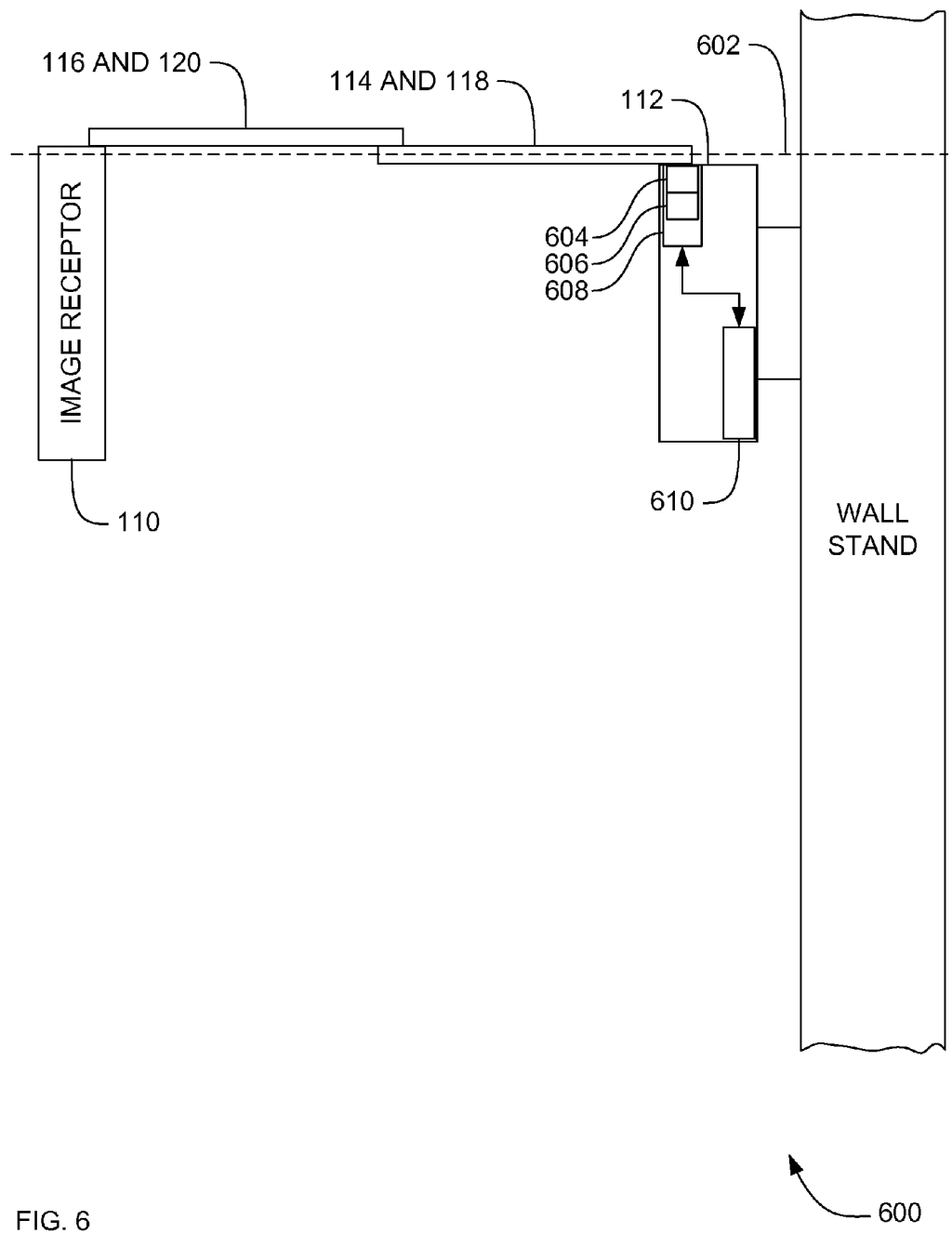
FIG. 6 is a side-view block diagram of an apparatus to operably couple a medical image receptor to a wallstand that includes one set of arms in parallel planes and in which arms of the apparatus are nearly fully extended.

FIG. 6 is a side-view block diagram of an apparatus 600 to operably couple a medical image receptor to a wallstand that includes one set of arms in parallel planes and in which arms of the apparatus are nearly fully extended. Apparatus 600 solves the need in the art for an improved range of motion of a medical image receptor that is operably coupled to a wallstand.

Apparatus 600 includes all of the same components as system 100 in FIG. 1, above. The articulated linkages 114, 118, 116 and 120 are positioned along a plane 602. In some embodiments, a clutch 604, an encoder 606, a drive 608 and a processor 610 are located in close proximity to at least one of the pivots, and the clutch 604 and the drive 608 are operably coupled to the pivot in close proximity to provide power to the pivots.

Figure 7:
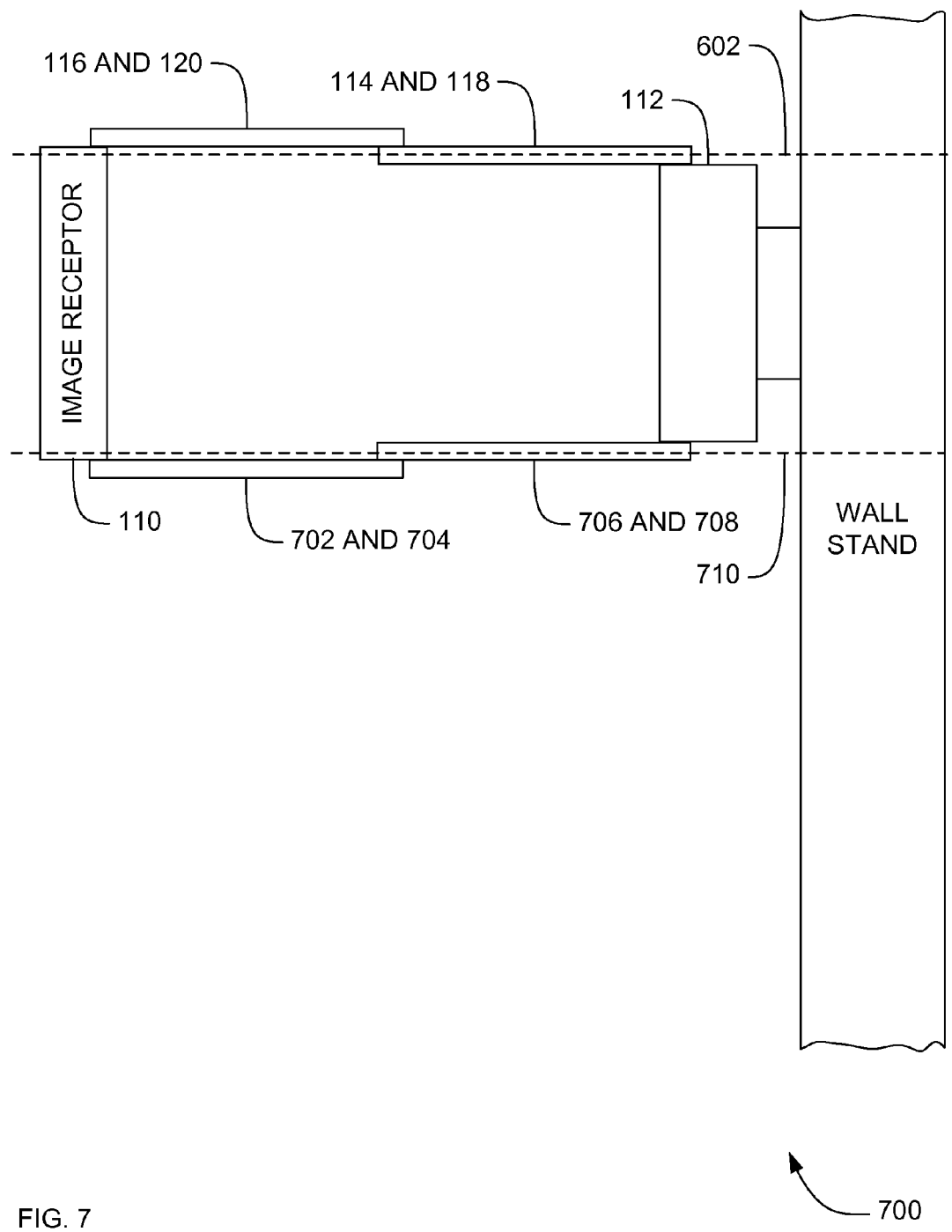
FIG. 7 is a side-view block diagram of an apparatus to operably couple a medical image receptor to a wallstand that includes two sets of arms in parallel planes and in which arms of the apparatus are nearly fully extended.

FIG. 7 is a side-view block diagram of an apparatus 700 to operably couple a medical image receptor to a wallstand that includes two sets of arms in parallel planes and in which arms of the apparatus are nearly fully extended. Apparatus 700 solves the need in the art for an improved range of motion of a medical image receptor that is operably coupled to a wallstand.

Apparatus 700 includes all of the same components as system 100 in FIG. 1, above. The articulated linkages 114, 118, 116 and 120 are positioned along a plane 602 that is parallel to articulated linkages 702, 704, 706 and 708 in a second plane 710. The articulated linkages 702, 704, 706 and 708 are substantially similar to the articulated linkages 114, 118, 116 and 120.

FIGS. 1-7 show that the arms and articulated linkages provide movement of the medical image receptor 110 relative to the wallstand 112 that is an in/out motion, a side-to-side motion and/or an oblique/twist rotation motion.

Figure 8:
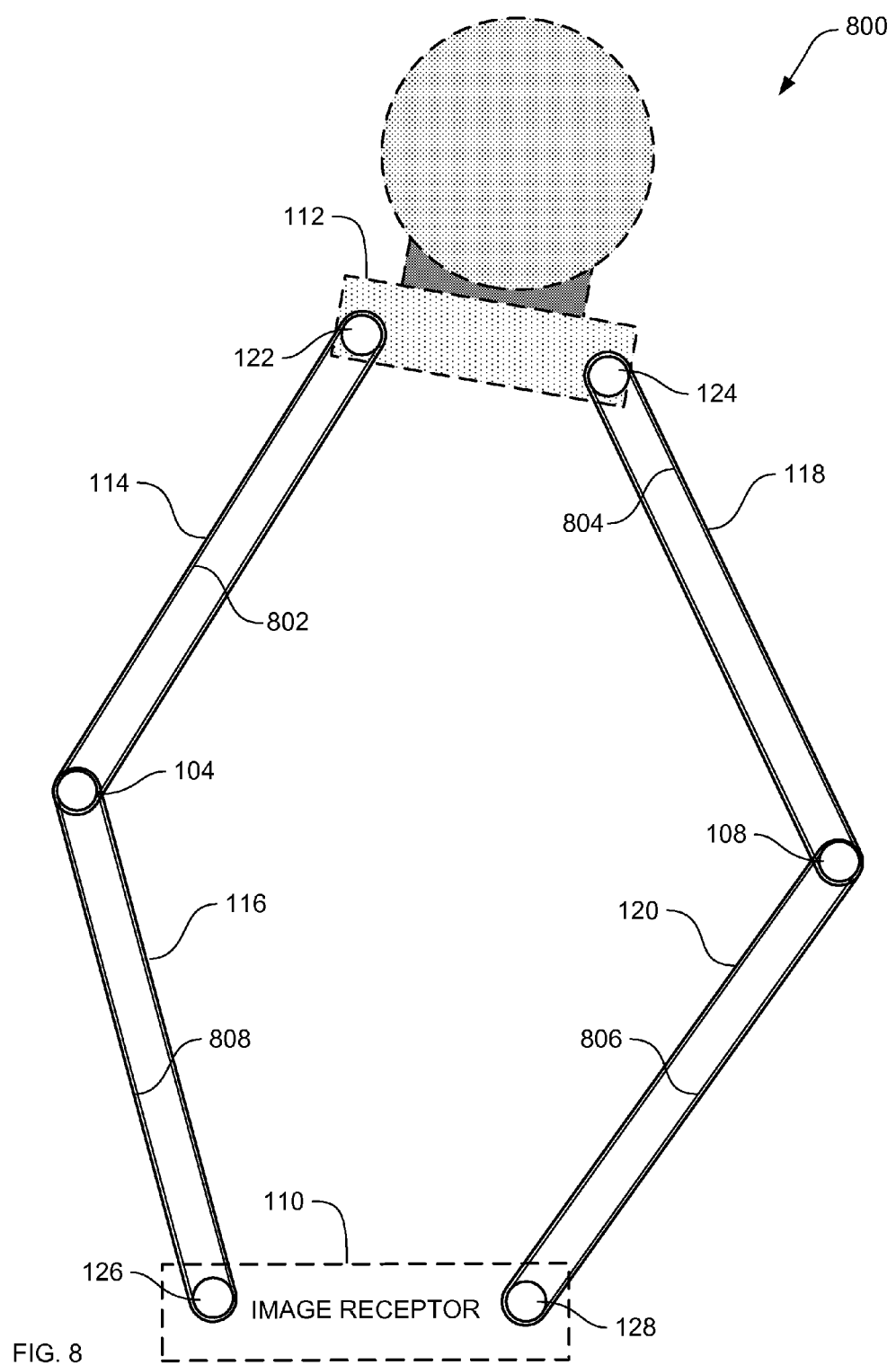
FIG. 8 is a top-view block diagram of an apparatus to operably couple a medical image receptor to a wallstand in which arms of the apparatus including apparatus to coordinate movements of the arms.

FIG. 8 is a top-view block diagram of an apparatus 800 to operably couple a medical image receptor to a wallstand in which arms of the apparatus including apparatus to coordinate movements of the arms. Apparatus 800 solves the need in the art for an improved range of motion of a medical image receptor that is operably coupled to a wallstand.

Apparatus 800 includes all of the same components as system 100 in FIG. 1, above, but with the addition of apparatus 802, 804, 806 and/or 808 to coordinate the movements of the arms. In some embodiments, apparatus 802, 804, 806 and 808 include chains and/or belts. In other embodiments, electric motors are included to coordinate the movements of the arms. In some embodiments, a clutch and a motor are located in close proximity to at least one of the pivots, and the clutch and motor are operably coupled to the pivot in close proximity to provide power to the pivots. In some embodiments, three clutch and motors are located in close proximity to three the pivots. For example, a clutch and motor are located in close proximity and operable to pivot 122, a clutch and motor are located in close proximity and operable to pivot 124 and a clutch and motor are located in close proximity and operable to pivot 128. In another example, a clutch and motor are located in close proximity and operable to pivot 122, a clutch and motor are located in close proximity and operable to pivot 124 and a clutch and motor are located in close proximity and operable to pivot 126. In yet another example, a clutch and motor are located in close proximity and operable to pivot 122, a clutch and motor are located in close proximity and operable to pivot 126 and a clutch and motor are located in close proximity and operable to pivot 128.

Method Embodiments

In the previous section, apparatus of the operation of an embodiment was described. In this section, the particular methods that can performed by a computer, processor, or microprocessor environment are described by reference to a flowchart.

Figure 9:
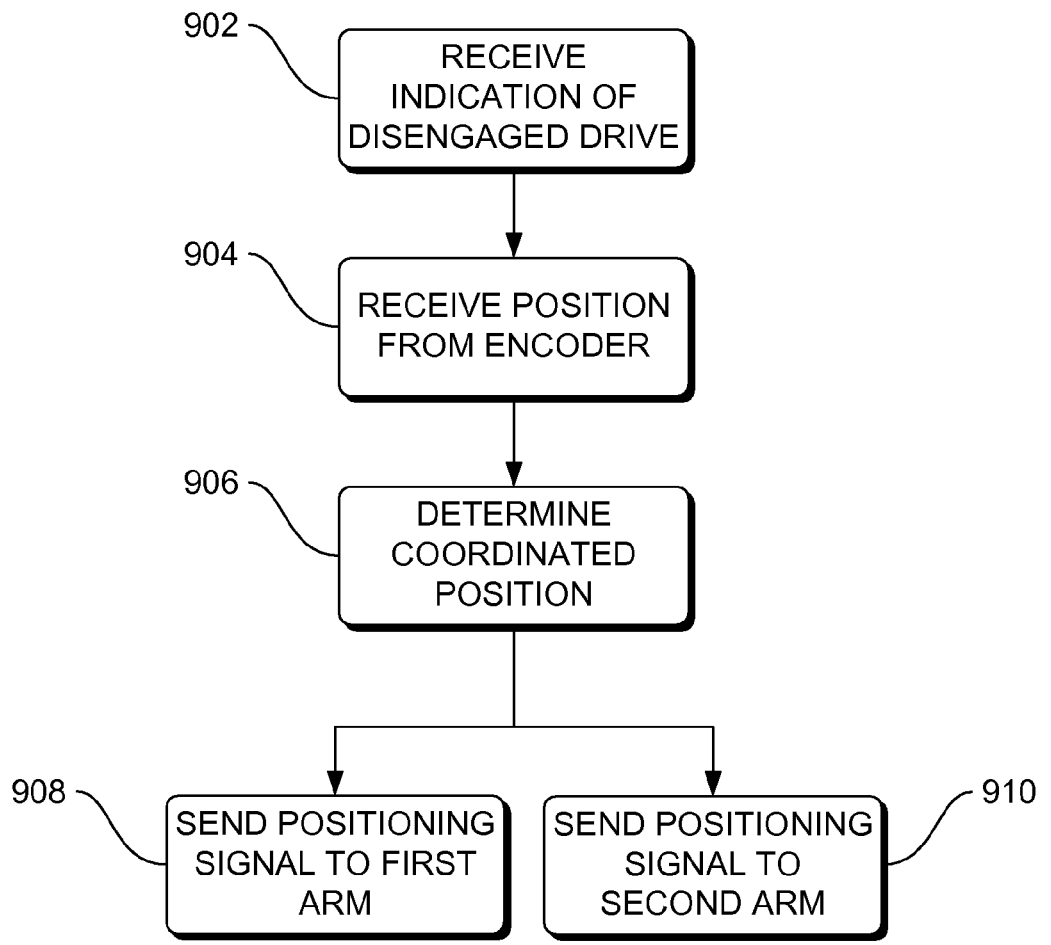
FIG. 9 is a flowchart of a method to position a medical X-ray image receptor, according to an embodiment.

FIG. 9 is a flowchart of a method 900 to position a medical X-ray image receptor, according to an embodiment. Method 900 assists manual movement and coordination of the medical image receptor.

Some embodiments of method 900 include receiving 902 an indication that a drive is disengaged from a wallstand apparatus. The drive has a clutch and an encoder. In some instances, the drive is disengaged by a human operating the drive clutch. As in FIGS. 1-7 above, the wallstand apparatus has a first articulated arm having at least three degrees of freedom, the first articulated arm being on a same plane as a second articulated arm. One example of the drive is an electric motor.

Some embodiments of method 900 include receiving 904 a position of the drive from the encoder.

Some embodiments of method 900 include determining 906 a coordinated position of the first articulated arm and the second articulated arm. A coordinated position is a position that has the same angular reference to fixed objects in the surrounding environment.

Some embodiments of method 900 include sending 908 at least one signal to a drive to move the first articulated arm into the coordinated position. The drive is operably coupled to the first articulated arm.

Some embodiments of method 900 include sending 910 at least one signal to a drive to move the second articulated arm into the coordinated position. The drive is operably coupled to the second articulated arm.

As the medical receptor is moved, method 900 the drive provides power assist and coordinated movement of the image receptor.

In some embodiments, method 900 is implemented as a computer data signal embodied in a carrier wave, that represents a sequence of instructions which, when executed by a processor, cause the processor to perform the respective method. In other embodiments, method 900 is implemented as a computer-accessible medium having executable instructions capable of directing a processor to perform the respective method. In varying embodiments, the medium is a magnetic medium, an electronic medium, or an optical medium.

Embodiments are described in terms of a computer executing computer-executable instructions. However, some embodiments can be implemented entirely in computer hardware in which the computer-executable instructions are implemented in read-only memory. Some embodiments can also be implemented in client/server computing environments where remote devices that perform tasks are linked through a communications network. Program modules can be located in both local and remote memory storage devices in a distributed computing environment.

Apparatus components of methods can be embodied as computer hardware circuitry or as a computer-readable program, or a combination of both. More specifically, in the computer-readable program embodiment, the programs can be structured in an object-orientation using an object-oriented language such as Java, Smalltalk or C++, and the programs can be structured in a procedural-orientation using a procedural language such as COBOL or C. The software components communicate in any of a number of means that are well-known to those skilled in the art, such as application program interfaces (API) or interprocess communication techniques such as remote procedure call (RPC), common object request broker architecture (CORBA), Component Object Model (COM), Distributed Component Object Model (DCOM), Distributed System Object Model (DSOM) and Remote Method Invocation (RMI).

CONCLUSION

An articulated multi-degree of freedom receptor arm for radiology room via a multilink closed mechanism is described. A technical effect of the mechanism is improved mobility of medical image receptors. Although specific embodiments are illustrated and described herein, it will be appreciated by those of ordinary skill in the art that any arrangement which is calculated to achieve the same purpose may be substituted for the specific embodiments shown. This application is intended to cover any adaptations or variations. For example, although described in X-ray terms, one of ordinary skill in the art will appreciate that implementations can be made in other medical imaging technologies that require the same of similar functions of mobility.

In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future medical image receptor, different wallstands, and new materials of construction of the arms.

The terminology used in this application meant to include image receptors and medical environments and alternate technologies which provide the same functionality as described herein.

We claim:

1. A medical imaging apparatus comprising:
   a medical image receptor;

a wallstand; and a mechanism having a first articulated arm, the first articulated arm being operably coupled to the wallstand by a first pivot and operably coupled to the medical image receptor by a second pivot, and having a third pivot between the first pivot and the second pivot that articulates the first articulated arm and that rotates in a same plane as the first pivot and the second pivot; and a second articulated arm, the second articulated arm being operably coupled to the wallstand by a fourth pivot and operably coupled to the medical image receptor by a fifth pivot, and having a sixth pivot between the fourth pivot and the fifth pivot that articulates the second articulated arm and that rotates in a same plane as the fourth pivot and the fifth pivot.

2. The medical imaging apparatus of claim 1, wherein the first articulated arm and the second articulated arm are planar members.

3. The medical imaging apparatus of claim 1, wherein the first articulated arm further comprises a seventh pivot between the first pivot and the second pivot and the second articulated arm further comprises an eighth pivot between the fourth pivot and the fifth pivot.

4. The medical imaging apparatus of claim 1, wherein the first articulated arm and the second articulated arm each further comprise:

three articulated members providing five degrees of freedom.

5. The medical imaging apparatus of claim 1, wherein the first articulated arm and the second articulated arm further comprise:

the first articulated arm and the second articulated arm being articulated in the same plane.

6. The medical imaging apparatus of claim 1, wherein the.

7. The medical imaging apparatus of claim 1, wherein the medical image receptor further comprises:

a medical X-ray image receptor.

8. An apparatus comprising:

medical image receptor;

a plurality of arms, each arm having two ends, each end having a rotatable joint, each arm have a rotatable joint between the rotatable joints at each end, each arm being rotatable in a plane that is unique and parallel to the plane of the other arms, one of the ends of each of the arms being connected to the medical image receptor.

9. The apparatus of claim 8, wherein each arm further comprises a second rotatable joint between the rotatable joints at each end that rotates in the same plane as the rotatable joints at each end.

10. The apparatus of claim 8, wherein the each arm further comprises:

three articulated members providing degrees of freedom.

11. The apparatus of claim 8, wherein the each arm further comprises:

each arm being articulated in the same plane.

12. The apparatus of claim 8, wherein each of the arms are planar members.

13. The apparatus of claim 8, wherein the medical image receptor further comprises:

a medical X-ray image receptor.

14. A computer-accessible medium having executable instructions to position a medical X-ray image receptor, the executable instructions capable of directing a processor to perform:

receiving an indication that a drive is disengaged from a wallstand apparatus, the drive having a clutch and an encoder, the wallstand apparatus having a plurality of arms, each arm having two ends, each end having a rotatable joint, each arm have a rotatable joint between the rotatable joints at each end, each arm being rotatable in a plane that is unique and parallel to the plane of the other arms, one of the ends of each of the arms being connected to the wallstand apparatus;

receiving a position from the encoder;

determining a coordinated position of the arms;

sending at least one signal to a drive that is operably coupled to each of the arms to move the arms into the coordinated position.

15. The computer-accessible medium of claim 14, wherein eacharm further comprises a second rotatable joint between the rotatable joints at each end that rotates in the same plane as the rotatable joints at each end.

16. The computer-accessible medium of claim 14, wherein each arm further comprises:

three articulated members providing five degrees of freedom.

17. The computer-accessible medium of claim 14, wherein each of the arms are planar members.

18. The computer-accessible medium of claim 14, wherein the medical image receptor further comprises:

a medical X-ray image receptor.

19. The computer-accessible medium of claim 14, wherein the drive further comprises:

an electric motor.

20. The computer-accessible medium of claim 14, wherein the coordinated position further comprises:

a position that has the same angular reference to fixed objects in the surrounding environment.

* * * * *